United States Patent [19]

Kirkpatrick

[11] 4,217,459
[45] * Aug. 12, 1980

[54] BENZYLTHIO-1,3,4-THIADIAZOL-2-YL UREAS

[75] Inventor: Joel L. Kirkpatrick, Overland Park, Kans.

[73] Assignee: Gulf Oil Corporation, Pittsburgh, Pa.

[*] Notice: The portion of the term of this patent subsequent to Jan. 3, 1995, has been disclaimed.

[21] Appl. No.: 952,504

[22] Filed: Oct. 18, 1978

Related U.S. Application Data

[60] Division of Ser. No. 827,489, Aug. 25, 1977, Pat. No. 4,141,717, which is a continuation-in-part of Ser. No. 701,262, Jun. 30, 1976, abandoned.

[51] Int. Cl.$^2$ ............................................ C07D 285/12
[52] U.S. Cl. .................................................... 548/140
[58] Field of Search ........................ 260/302 D; 71/90

[56] References Cited

U.S. PATENT DOCUMENTS

| | | | |
|---|---|---|---|
| 3,717,651 | 2/1973 | Pilgram et al. | 71/90 |
| 4,056,382 | 11/1977 | Soper | 71/90 |
| 4,066,436 | 1/1978 | Kirkpatrick | 71/90 |

FOREIGN PATENT DOCUMENTS 1816568 11/1970 Fed. Rep. of Germany .
1297147 11/1972 United Kingdom .

OTHER PUBLICATIONS

C. Metzger et al., Chem. Abst., 82:57702c (1975), Herbicidal 1,3,4-thiadiazolylureas.

*Primary Examiner*—Donald G. Daus
*Assistant Examiner*—M. C. Eakin
*Attorney, Agent, or Firm*—Carl A. Cline

[57] ABSTRACT

Weeds are selectively controlled in soybean fields by post-emergent application of a compound having the structural formula

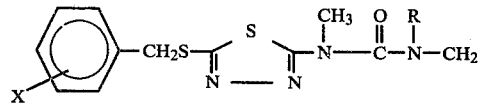

in which X represents bromo, fluoro, cyano or trifluoromethyl and R is hydrogen or methyl.

5 Claims, No Drawings

BENZYLTHIO-1,3,4-THIADIAZOL-2-YL UREAS

This application is a division of U.S. patent application Ser. No. 827,489, filed Aug. 25, 1977, now U.S. Pat. 4,141,717, which is a continuation-in-part of copending U.S. patent application Ser. No. 701,262, filed on June 30, 1976, now abandoned.

DESCRIPTION OF THE INVENTION

BACKGROUND OF THE INVENTION

In the present state of the art of soybean culture in the United States it has become common practice to employ one of two or three available pre-emergent herbicides for weed control. In general this method gives relatively good control of grassy weeds. However, a number of broadleaf weeds benefit from the reduced competition from the grasses and create severe problems later in the growing season, sometimes sufficient to prevent the harvesting of the soybeans.

Although more effective, broader spectrum pre-emergent herbicides have been sought for use with soybeans, this approach to the problem has not been successful because of the sensitivity of soybeans to herbicides. An alternative method of controlling broadleaf weeds is to employ a post-emergent herbicide shortly after emergence of the weeds. This method is not yet a widely accepted practice because of a shortage of suitable herbicides. No more than two herbicides have given consistently acceptable results in the midwestern U.S. and cocklebur has only been controlled by applications that also caused substantial injury to soybeans.

(See *Successful Farming* vol. 74 No. 4, page C12, February 1976.)

Just as soybeans are known to be sensitive to herbicides, peanuts are well known to be relatively insensitive, and permit the use of a much wider variety of herbicides. However, in the southeastern U.S. a herbicide-resistant weed has become a pest in peanuts in spite of the use of herbicides, probably benefiting from reduced competition. This weed, commonly called sicklepod has spread widely and is now probably the worst weed in soybeans in southeastern U.S. (See *Weeds Today*, Spring 1976, pages 12–14.) This weed problem is being attacked by means of mechanical cultivation and a variety of both pre-emergent and post-emergent herbicides. However, erratic results have been obtained with herbicides under the various soil and climatic conditions which exist in the area.

SUMMARY OF THE INVENTION

I have discovered that broadleaf weeds including cocklebur and sicklepod can be selectively controlled in soybean fields by applying post-emergently an effective amount, which may be less than one-half pound per acre, sufficient to control weeds but insufficient to cause substantial permanent injury to soybeans, of a compound having the general structural formula

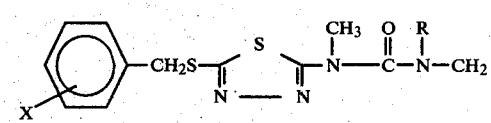

in which X represents a substituent selected from the group consisting of bromo, fluoro, cyano and trifluoromethyl and R is hydrogen or methyl. In general, compounds with substituents in the meta position exhibit greater herbicidal activity and are usually preferred for that reason.

DETAILED DESCRIPTION (1) Synthesis of the Herbicides

The general method of synthesis of the herbicides employed in the method of this invention is outlined below:

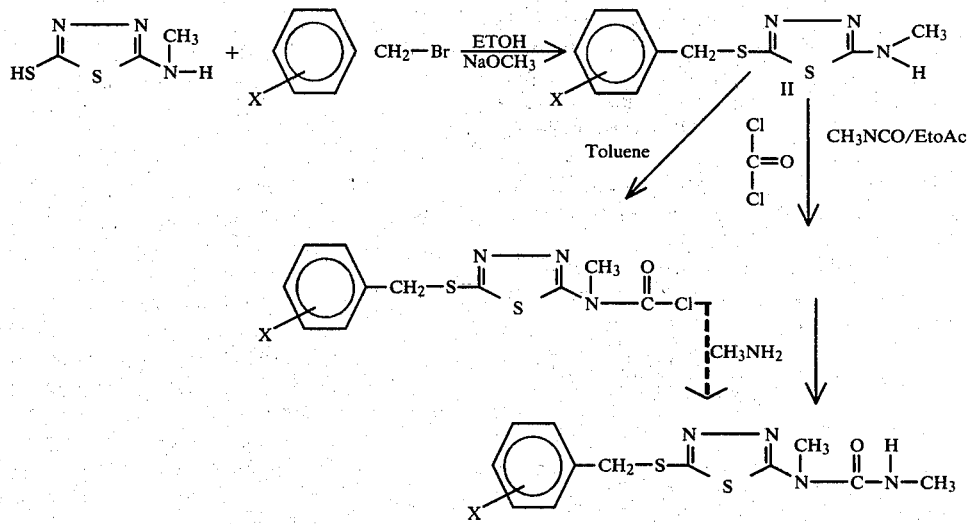

The following procedure, directed to the synthesis of an unsubstituted benzyl compound is a representative procedure which is presented for purposes of illustration.

Preparation of 2-methylamino-5-benzylthio-1,3,4-thiadiazole

To a solution of sodium ethoxide in ethanol (prepared by adding 13.5 g of anhydrous sodium methoxide to 300 ml of absolute ethanol) was added 31 g of 2-methylamino-5-1-mercapto-1,3,4-thiadiazole. After stirring for 15 min. at room temperature, 36 g of benzyl bromide was added to the homogeneous solution and the reaction heated to reflux for 4 hrs. At the end of the reflux period, most of the ethanol was removed at reduced pressure, water was added and the reaction extracted with ethyl acetate, which was washed with water and saturated NaCl, then dried over $Na_2SO_4$. Removal of the solvent gave a viscous oil which was crystallized from a mixture of ether and petroleum ether to give 29.7 g of 2-methylamino-5-benzylthio-1,3,4,-thiadiazole, MP 87°–89° C.

Preparation of
1,3-Dimethyl-3-(5-benzyl-thio-1,3,4-thiadiazol-2-yl)urea

To a solution of 2-methylamino-5-benzylthio-1,3,4-thiadiazole (4.0 g) in ethyl acetate (100 ml) was added 1.5 g of methyl isocyanate. The reaction was stirred at room temperature for 2 hrs. then heated at reflux for an additional 2 hrs. The product, 1,3-dimethyl-3-(5-benzylthio-1,3,4-thiadiazol-2-yl)urea, crystallized upon the addition of petroleum ether, was collected, washed with ether and dried to give 4.7 g, MP 139°–142° C.

Preparation of
1,3,3-Trimethyl-3-(5-p-bromobenzylthio-1,3,4-thiadiazol-2-yl)urea A solution of 20 g (0.063 mol) of 2-methylamino-5-(4-bromobenzylthio)-1,3,4-thiadiazole in 300 ml of toluene was saturated with dry HCl at room temperature with stirring. To this suspension was added 150 ml of a 12.5% solution of phosgene in benzene (MCB), and the reaction was heated at reflux temperature for 2 hrs. After cooling, a small amount of insoluble material was removed by filtration and an excess of 40% aqueous dimethylamine was added. The reaction was allowed to stir at room temperature for 1½ hr., then was washed successively with dilute hydrochloric acid, water and saturated aqueous sodium chloride and was dried over anhydrous sodium sulfate. Removal of the solvent gave a residue which was crystallized from a mixture of ether and petroleum ether: yield 18.5 g, MP67°–69° C. Recrystallization from ether-petroleum ether gave an analytical sample, MP 72°–74° C.

In the following table are listed compounds which have been made by means of procedures of the type illustrated above.

TABLE 1

Compounds of the Formula $$\underset{X}{\bigodot}-CH_2S-\underset{N\underline{\quad\quad}N}{\overset{S}{\underset{\|}{\diagdown\diagup}}}-\underset{\underset{N}{\overset{CH_3O}{|}}}{\overset{CH_3}{|}}\underset{\underset{CH_3}{|}}{\overset{R}{\underset{\|}{C}}}-N-CH_3$$

| Compound No. | X | R | m.p. (° C.) |
|---|---|---|---|
| 1 | m-cyano | H | 104–106 |
| 2 | p-bromo | H | 117–119 |
| 3 | m-fluoro | H | 115–118 |
| 4 | p-fluoro | H | 168–171 |
| 5 | m-trifluoromethyl | H | 118–119 |
| 6 | p-nitro | H | 168–171 |
| 7 | 2,6-dichloro | H | 210–213 |
| 8 | m-fluoro | $CH_3$ | oil |
| 9 | p-bromo | $CH_3$ | 72–74 |
| 10 | m-bromo | $CH_3$ | 62–62 |

Compounds numbered 6 and 7 above are unsuitable for use in the present invention and are only included to demonstrate the narrow limits of suitability. Compound No. 6 is not sufficiently effective against such weeds as pigweed, velvet leaf and morning glory, for example, when applied at rates low enough to avoid substantial permanent injury to soybeans. Compound No. 7 has so little phytotoxicity of any kind that it appears to have no practical utility as an agricultural herbicide.

It is generally true of selective herbicides that selectivity is more evident and efficacy is reduced at lower application rates. Many of the thiadiazoleurea herbicides, however are almost totally non-selective and merely exhibit reduced efficacy at lower application rates. Such compounds may find utility as industrial herbicides. The herbicides of the present invention are unusual in that they are selective, exhibiting both safety on soybeans and high efficacy at low application rates, which may be less than one-half pound per acre. Compound No. 3 is unique with respect to safety on soybeans and efficacy on weeds over a broad range of application rates. In greenhouse tests these properties have been maintained at application rates of from one sixteenth pound to two pounds per acre.

Compound No. 8 has less efficacy than Compound No. 3, but is also safe on soybeans and in some instances may be preferred because it is exceptionally easy to formulate as an emulsifiable solution.

Compound No. 9 and 10 have efficacy and selectivity over a narrower range of application rates than Compound No. 3 and are also less effective on sicklepod. However, both of these compounds may be used to kill several of the weeds commonly associated with soybeans, without substantial permanent injury to the crop.

(2) Weed Control in Presence of Soybeans

Post-emergent control of weeds in the presence of soybeans may be demonstrated in the greenhouse by means of the procedure outlined below.

Procedure

Greenhouse potting soil is placed in rectangular trays, commonly called "flats" made of expanded polystyrene and measuring about 12 in. by 10 in. by 3 in. in depth. Seeds of the test species are planted in the soil and the planted flats are placed on the greenhouse benches where temperature and watering are regulated to provide good growth conditions. At about 12 days after planting when all plants have emerged and have exhibited normal growth, the plants are sprayed with an aqueous dispersion of herbicide at a spray volume of 40 ga./A. Spray mixtures may be made conveniently by diluting with water an emulsifiable concentrate containing, besides the herbicide, a solvent such as a mixture of three parts xylene and one part isophorone, along with about one part of a commercial emulsifier consisting of a blend of anionic and nonionic surface active agents.

At two to three weeks after spraying the condition of the plants is observed and rated on a scale of 1 to 10, ranging from observable temporary injury to total kill. Where no injury is observable, the rating is zero. Representative results are presented for illustrative purposes in the following table. Where two scores are recorded for the same species and rate, they represent results obtained in two tests, one in early spring and one in late spring or early summer.

TABLE 2
Results of Greenhouse Tests

| Species | Appl. Rate oz./A | No. 1 | No. 2 | No. 3 | No. 4 | No. 5 | No. 8 | No. 9 | No. 10 |
|---|---|---|---|---|---|---|---|---|---|
| Pigweed | 8 |  | 10 | 10 | 10 | 10 | 10 | 10 | 10 |
|  | 4 | 9 | 10 | 10 | 8 | 10 | 10 | 10 | 10 |
|  | 2 |  |  | 10 |  |  | 6 | 10 | 10 |
|  | 1 |  |  | 10 |  |  |  | 10 | 10 |
| Smartweed | 8 |  | 10 | 10 | 10 | 10 | 10 | 10 | 10 |
|  | 4 | 10 | 10 | 10 | 10 | 10 | 10 | 10 | 10 |
|  | 2 | 10 | 10 | 10 |  | 10 | 10 | 10 | 10 |
|  | 1 | 10 | 10 | 8 |  | 10 |  | 10 | 7 |
| Velvet leaf | 8 |  | 10 | 10 | 8 | 10 | 10 | 10 | 10 |
|  | 4 | 10 | 9 | 10 | 10 | 10 | 10 | 10 | 10 |
|  | 2 | 9 | 8 | 10 |  | 8 | 8 | 10 | 7 |
|  | 1 | 6 | 7 | 7 |  | 8 |  | 7 | 3 |
| Jimson weed | 8 |  | 10 | 10 | 10 | 10 | 10 | 10 | 10 |
|  | 4 | 10 | 10 | 10 | 10 | 10 | 10 | 10 | 10 |
|  | 2 | 10 | 10 | 10 |  | 10 | 10 | 10 | 10 |
|  | 1 | 10 | 10 | 10 |  | 10 |  | 10 | 7 |
| Morning glory | 8 |  | 10 | 10 | 8 | 10 | 9 | 10 | 10 |
|  | 4 | 9 | 9 | 8,10 | 8 | 10 | 3 | 10 | 10 |
|  | 2 | 7 | 8 | 8,10 |  | 10 | 2 | 10 | 6 |
|  | 1 | 4 | 3 | 6,8 |  | 6 |  | 7 | 3 |
| Cocklebur | 8 |  | 8 | 10 | 8 | 10 | 10 | 10 | 10 |
|  | 4 | 10 | 10 | 10,10 | 10 | 10 | 10 | 10 | 10 |
|  | 2 | 7 | 10 | 10,10 |  | 10 | 10 | 10 | 6 |
|  | 1 | 10 | 10 | 10,7 |  | 10 |  | 10 | 4 |
| Beggarweed | 8 |  | 10 | 10 |  | 10 |  |  |  |
|  | 4 | 10 | 10 | 10 |  | 10 |  |  |  |
|  | 2 | 10 | 10 | 10 |  | 10 |  |  |  |
|  | 1 | 10 | 6 | 5 |  | 8 |  |  |  |
| Sesbania | 8 |  | 10 | 10,10 |  | 10 |  | 10 | 10 |
|  | 4 | 10 | 10 | 10,10 |  | 10 |  | 10 | 10 |
|  | 2 | 10 | 10 | 10,10 |  | 10 |  | 7 | 6 |
|  | 1 | 8 | 6 | 5,8 |  | 6 |  | 4 | 2 |
| Sicklepod | 8 |  | 10 | 10,10 |  | 10 |  | 10 | 10 |
|  | 4 | 10 | 10 | 10,10 |  | 10 |  | 8 | 10 |
|  | 2 | 10 | 10 | 10,10 |  | 10 |  | 7 | 4 |
|  | 1 | 8 | 5 | 10,7 |  | 10 |  | 5 | 1 |
| Prickly sida | 8 |  | 10 | 10 |  | 10 |  | 10 | 10 |
|  | 4 | 10 | 10 | 8 |  | 10 |  | 10 | 10 |
|  | 2 | 5 | 8 | 7 |  | 10 |  | 10 | 10 |
|  | 1 | 2 | 6 | 4 |  | 8 |  | 10 | 6 |
| Soybeans | 8 |  | 4,3 | 2 | 1 | 4,8 | 1 | 3 | 7 |
|  | 4 | 1,4 | 2,2 | 2,1 | 1 | 2,5 | 1 | 2 | 2 |
|  | 2 | 2,2 | 1 | 1,0 |  | 5,2 | 1 | 2 | 1 |
|  | 1 | 0,1 | 1,1 | 1,0 |  | 1 |  | 1 | 1 |

The amount of herbicide which is effective against plants grown under excellent conditions may be judged by examination of the data presented above. It is understood by those skilled in the art that plants grown under adverse conditions may require more herbicide. It also a common practice to use less efficient methods of application to prevent spray from drifting in the wind. Allowance must therefore be made, according to conventional practice, for spray that does not reach the foilage, but falls on the ground and is wasted. As indicated by the data tabulated above, an effective amount of herbicide may be less than a half pound per acre if applied efficiently to plants grown under ideal growing conditions. Inefficient application and use on mature plants or more resistant vegetation grown under adverse conditions may require more than double the proper amount as indicated in the table. It is well understood by workers in the art that maintenance of the best possible growing conditions for the soybeans and reduction of competition from weeds by application of herbicide early in the growing season will result in the greatest improvement of crop yields and with the use of less herbicide.

Because of the high degree of efficacy of the compounds employed in the method of the invention, it is preferred to apply the compounds in inert diluents so as to obtain more even distribution. Water and inert powdered solids are preferred as diluents, according to conventional practice.

I claim:
1. 1,3-Dimethyl-3-(5-m-cyanobenzylthio-1,3,4-thiadiazol-2-yl)urea.
2. 1,3-Dimethyl-3-(5-m-fluorobenzylthio-1,3,4-thiadiazol-2-yl)urea.
3. 1,3-Dimethyl-3-(5-m-trifluoromethylbenzylthio-1,3,4-thiadiazol-2-yl)urea.
4. 1,1,3-Trimethyl-3-(5-m-fluorobenzylthio-1,3,4-thiadiazol-2-yl)urea.
5. 1,1,3-Trimethyl-3-(5-m-bromobenzylthio-1,3,4-thiadiazol-2-yl)urea.

* * * * *

UNITED STATES PATENT OFFICE
CERTIFICATE OF CORRECTION

Patent No. 4,217,459                 Dated August 12, 1980

Inventor(s) Joel L. Kirkpatrick

It is certified that error appears in the above-identified patent and that said Letters Patent are hereby corrected as shown below:

In the Abstract the portion of the structural formula reading should read

Column 2, line 15, the portion of the general structural formula reading

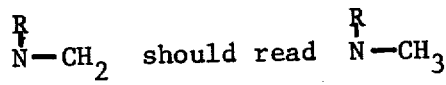  should read

*Signed and Sealed this*

*Twenty-eighth* Day of *October 1980*

[SEAL]

Attest:

SIDNEY A. DIAMOND

Attesting Officer                Commissioner of Patents and Trademarks